United States Patent [19]

Garthoff et al.

[11] Patent Number: 4,582,840
[45] Date of Patent: Apr. 15, 1986

[54] 1,4-DIHYDRO-2,6-DIMETHYL-4-NITROPHE-NYL-3,5-PYRIDINEDICARBOXYLIC ACID ESTERS USEFUL FOR TREATING RENAL INSUFFICIENCY

[75] Inventors: Bernward Garthoff, Hilden; Stanislav Kazda, Wuppertal; Andreas Knorr, Wuppertal; Günter Thomas, Wuppertal, all of Fed. Rep. of Germany

[73] Assignee: Bayer Aktiengesellschaft, Leverkusen, Fed. Rep. of Germany

[21] Appl. No.: 726,879

[22] Filed: Apr. 25, 1985

Related U.S. Application Data

[63] Continuation of Ser. No. 477,469, Mar. 21, 1983, abandoned.

[30] Foreign Application Priority Data

Apr. 6, 1982 [DE] Fed. Rep. of Germany ....... 3212736

[51] Int. Cl.⁴ ................. C07D 213/55; A61K 31/455
[52] U.S. Cl. ..................................... 514/356; 546/321
[58] Field of Search ......................... 546/321; 514/356

[56] References Cited

U.S. PATENT DOCUMENTS 3,485,847 12/1969 Bossert et al. ...................... 546/321
4,412,986 11/1983 Kawata et al. ...................... 514/356
4,435,409 3/1984 Leibowitz et al. .................. 514/356

FOREIGN PATENT DOCUMENTS 3212736 10/1983 Fed. Rep. of Germany ...... 514/356

Primary Examiner—Alan L. Rotman
Attorney, Agent, or Firm—Sprung Horn Kramer & Woods

[57] ABSTRACT

A method of combating a disorder of the salt balance in a patient afflicted therewith comprising administering to such patient a salt-balance restoring effective amount of a vasodilating 1,4-dihydropyridine of the formula

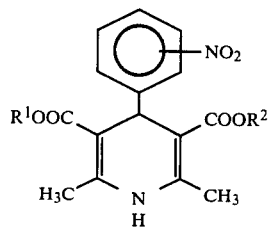

in which $R^1$ and $R^2$ each independently is alkyl with 1 to 4 carbon atoms, and the nitro radical is in the ortho- or meta-position of the phenyl radical.

The salt balance disorder may accompany the hypertensive disease or may also be aggravated by administering to such a patient a hypertension reducing agent.

7 Claims, No Drawings

1,4-DIHYDRO-2,6-DIMETHYL-4-NITROPHENYL-3,5-PYRIDINEDICARBOXYLIC ACID ESTERS USEFUL FOR TREATING RENAL INSUFFICIENCY

This is a continuation of application Ser. No. 477,469, filed Mar. 21, 1983, now abandoned.

The present invention relates to the use of 1,4-dihydropyridines, some of which are known, in combating disorders of the salt balance of the body, in particular their use in medicaments having a salidiuretic action.

It has already been disclosed that 1,4-dihydropyridines have vasodilative actions and can be used as coronary agents and blood pressure agents (compare German Offenlegungsschrift No. 1,670,827, British Pat. No. 1,173,862, German Offenlegungsschrift No. 2,117,571, British Pat. No. 1,358,951, German Offenlegungsschrift No. 2,549,568 and British Pat. No. 1,516,793, and the publications by Lederballe-Pedersen et al., Acta.Med.Scand. (Suppl.) 625, 65 (1979); and Vogt. A. et al., Arzneim.-Forsch. (Drug-Res.) 30, 2162 (1980)).

It is also known that vasodilative medicaments have for years been of significant importance in the therapy of hypertension (compare Opie, L. H., Brit. Med. J. 8175, 966 (1980)). The known active compounds hydralazine and its derivatives (compare Koch-Weser, J.Arch.Int. Med. 1933, 1017 (1974) and DeQuattro, V. et al., M. J. Antonaccio (ed.), Cardiovascular pharmacology, Raven Press, New York, 1977) and also minoxidil (compare Gilmore, E. et al., N.Engl.J.Med. 282, 521 (1970)) effect therapeutic lowering of blood pressure by reducing the increased peripheral resistance of hypertension. However, their broad application as mono-therapeutic agents in the long-term treatment of hypertension is impeded by the disadvantage of an undesirable restriction on the renal function, which as a rule manifests itself in a reduction in the excretion of sodium and water. During long-term use, the resulting retention of sodium and water erodes the anti-hypertensive activity of the substances, and in many patients can lead to oedema formation and an increase in body weight (compare Finnerty, F. A., Am. Heart J. 81, 563 (1971) and McMahon, G., Futura Publ. Co., Inc. New York 1978, page 8).

Possible additional medication with diuretic agents or saluretic agents, which are frequently used in the therapy of hypertension (compare Wilburn, R. L. et al., Cirkulation 52, 706 (1975) and Wilkinson, E. L. et al., J. Clin. Invest. 31, 872 (1952)), helps only in some of the cases, so that numerous cases of discontinuation of therapy and substantial medical helplessness may arise.

The present invention relates to 1,4-dihydropyridines of the general formula (I)

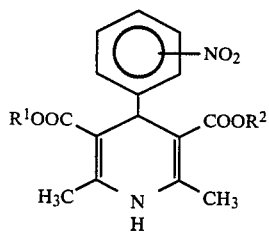

(I)

in which $R^1$ and $R^2$ are identical or different and each represents alkyl with 1 to 4 carbon atoms, and the nitro radical is in the ortho- or meta-position of the phenyl radical, for use as medicaments having a salidiuretic action.

The use of these dihydropyridines having salidiuretic properties in combating hypertension accompanied by a disturbed salt balance is of particular interest.

The compounds dimethyl 1,4-dihydro-2,6-dimethyl-4-(o-nitrophenyl)-pyridine-3,5-dicarboxylate (nifedipine), 3-methyl 5-butyl 1,4-dihydro-2,6-dimethyl-4-(o-nitrophenyl)-pyridine-3,5-dicarboxylate (nisoldipine) and 3-methyl 5-ethyl 1,4-dihydro-2,6-dimethyl-4-(m-nitrophenyl)-pyridine-3,5-dicarboxylate (nitrendipine) are particularly suitable for this purpose.

In view of the prior art, it could not be expected that, in contrast to the vasodilatives known hitherto, the dihydropyridines according to the invention do not produce retention but increased secretion of sodium and water. It is also surprising that precisely the selected dihydropyridines according to the invention have these advantageous salidiuretic properties, while other chemically similar dihydropyridines, such as, for example, the known nimodipine (compare German Offenlegungsschrit No. 2,815,578) do not display this action. The dihydropyridines selected according to the invention thus represent an unexpected enrichment of the therapy of hypertension.

The compounds according to the invention and processes for their preparation are known (compare German Offenlegungsschrift No. 1,792,764 and German Offenlegungsschrift No. 2,117,571).

The compounds can be converted in a known manner into the customary formulations, such as tablets, capsules, dragees, pills, granules, syrups, emulsions, suspensions and solutions, using inert, non-toxic, pharmaceutically suitable excipients or solvents. The therapeutically active compound should in each case be present in a concentration of 0.5 to 90% by weight of the total mixture, that is to say in amounts which are sufficient to achieve the required dosage.

In the case of parenteral administration, amounts of 0.05 to 10 mg/kg of body weight, in particular 0.1 to 2 mg/kg of body weight, are preferably administered to achieve effective results. For oral administration, the dosage is preferably 0.1 to 10 mg/kg of body weight per day, in particular 0.2 to 5 mg/kg of body weight per day.

If required, the amounts administered may deviate from those above, and in particular as a function of the body weight and the particular type of administration route. The time of administration and the interval between individual administrations of particular formulations may also result in a modification of the dosage. It may be sufficient either to manage with less than the above-mentioned minimum amount or, in other cases, necessary to exceed the upper limit of the amount mentioned.

The agents which can be used according to the invention are prepared, for example, by extending the active compound with solvents and/or excipients, if necessary using emulsifiers and/or dispersing agents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example highly disperse silicic acid and silicates), sugars (for example sucrose, lactose and dextrose), emulsifiers, such as non-ionic and anionic emulsifiers (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium lauryl sulphate).

Administration is effected in the customary manner, preferably enterally or parenterally, in particular orally.

In the case of enteral administration, tablets can of course also contain, in addition to the excipients mentioned, additives such as sodium citrate, calcium carbonate and dicalcium phosphate, together with various additional substances, such as starch, preferably potato starch, gelatine and the like. Lubricants, such as magnesium stearate, sodium lauryl sulphate and talc can also be used for tablet-making. In the case of aqueous suspensions and/or elixirs intended for oral administration, the active compounds may be mixed with various flavour improvers or colorants, in addition to the abovementioned auxiliaries.

Solutions of the active compound using suitable liquid excipients can be used for parenteral administration.

Examples of pharmaceutical formulations

1. Soft gelatine capsules containing 5 mg of active compound per capsule
For about 10,000 capsules, a solution having the following composition is prepared:

| nitrendipine (active compound) | 58.8 g |
| glycerol | 240.0 g |
| polyethylene glycol 400 | 3,833.2 g |
| water | 400.0 g |
| | 4,532.0 g |

Soft gelatine oblong capsules 6 minims in size are filled with the solution in a manner which is known per se. The capsules are suitable for chewing or swallowing.

2. Tablets, coated tablets or dragees containing 10 mg of active compound:
The following amounts relate to the production of 100,000 tablets or cores:

| dihydropyridine (finely ground active compound) | 1.00 kg |
| Lactose | 10.25 kg |
| starch | 2.70 kg |
| microcrystalline cellulose | 2.70 kg |

The above constituents are mixed in a planetary mixer, and are then mixed with a solution prepared from:

| polyvinylpyrrolidone (average molecular weight 25,000) | | 1.20 kg |
| polysorbate 80 USP (Tween 80 ®) and | | 0.06 kg |
| water | about | 4.00 kg | and the mixture is granulated in a manner which is known per se, by grating the moist composition and drying it.

| Magnesium stearate | 0.09 kg | in then added.

The finished tablet mixture weighing 18 kg is pressed to give convex tablets weighing 180 mg and 8 mm in diameter.

The tablets can be coated and converted into dragees in a manner which is known per se.

3. Drops containing 4 mg of active compound per ml:
The following solution is prepared:

| | For drops containing 4 mg per ml |
|---|---|
| nitrendipine (active compound) | 4.0 g |
| 96% strength ethanol | 450.0 g |
| liquid aroma | 6.0 g |
| methylparaben | 1.0 g |
| polyethylene glycol 400 | 50.0 g |
| 50% strength sugar syrup | 400.0 g |
| food coloring (Yellow Orange S) | 0.6 g |
| water to | 1,000.0 ml |

The active compound, methylparaben and aroma are dissolved at room temperature. The polyethylene glycol 400 and the 50% strength sugar syrup are then slowly added, while stirring, the colorant is dissolved and the mixture is made up to 1,000 ml with water.

Small brown bottles are filled with the solution, it also being possible to add sweeteners if necessary.

4. Syrup containing 10 mg of active compound per 10 ml:

| nitrendipine (active compound) | 1.0 g |
| methylparaben | 1.0 g |
| 96% strength ethanol | 250.0 g |
| liquid aroma | 4.0 g |
| polyethylene glycol 400 | 100.0 g |
| glycerol | 250.0 g |
| 50% strength sugar syrup | 300.0 g |
| food coloring (Yellow Orange S) | 0.5 g |
| water to | 1,000.0 ml |

The syrup is prepared in a manner analogous to that in Example 3.

Surprisingly, a qualitative difference in respect of the renal excretory capacity in comparison with commercially available vasodilative antihypertensive agents was found in pathophysiological animal models under conditions close to clinical conditions. In these animal experiments, nifedipine, nitrendipine and nisoldipine cause a dose-dependent increase in the excretion of sodium and water. This effect occurs both in normotensive subjects and in hypertensive subjects within the range of hypotensive doses. In contrast, minoxidil and hydralazine cause a reduction in the excretion of sodium and water within the hypotensive dose range, as is known from their clinical use.

The usefulness of the dihydropyridines according to the invention is that, unlike other vasodilators, these compounds can be used not only in combination with a diuretic in long-term therapy. The compounds according to the invention themselves improve the renal excretory capacity, without other diuretic active compounds having to be present. As vasodilators in monotherapy, they can therefore also advantageously be successfully used as antihypertensive agents and salidiuretic agents on patients with hypertension for whom the use of vasodilators has till now presented a risk or for whom simultaneous treatment with diuretic agents presented problems.

The following test results show, by way of example, the surprising salidiuretic actions of the compounds according to the invention in comparison with known, commercially available vasodilators.

Test methods (a) Diuretic action on rats

Normotensive or spontaneously hypertensive rats receive 30 ml/kg of 0.9% strength saline solution perorally. Control animals additionally receive 5 ml/kg of 0.5% strength Tylose solution perorally. The animals to be treated receive the same amount of Tylose solution containing the test substance. The solutions are administered intragastrically by means of a stomach tube. The animals are then placed in metabolism cages and the excretion of urine and electrolytes over a period of 6 hours is determined. The concentration of $Na^+$ and $K^+$ is determined by flame photometry.

(b) Antihypertensive action on rats

After recording a starting blood pressure value, normotensive or spontaneously hypertensive rats are treated orally with Tylose solution or with Tylose solution containing test substance by means of a stomach tube. The blood pressure is then measured 1, 2, 4 and 6 hours after the administration. The maximum effect (lowest systolic blood pressure value) for the particular control or treatment group during the 6-hour observation period is determined.

TABLE 1

Diuretic action of nitrendipine, nifedipine and nisoldipine in comparison with other commercially available vasodilators (total excretion over 6 hours after administration) on normotensive rats dosed with saline solution.
Data: $\bar{x} \pm$ SEM of in each case n = 6.

| Substance | Dose mg/kg perorally | Urine volume ml/kg/6 hour | Excretion of sodium μmol/kg/6 hour | Excretion of potassium μmol/kg/6 hour |
|---|---|---|---|---|
| Control | 0 (NaCl) | 23.0 ± 1.41 | 1524 ± 154.8 | 676 ± 61.8 |
| Nitrendipine | 0.315 | 19.2 ± 1.33 | 1430 ± 77.7 | 549 ± 43.2 |
|  | 1.0 | 27.3 ± 1.11 | 1883 ± 221.8 | 697 ± 33.7 |
|  | 3.15 | 27.6 ± 0.44 | 2296 ± 162.9 | 779 ± 48.6 |
|  | 10.0 | 28.2 ± 2.19 | 2308 ± 309.5 | 595 ± 80.8 |
|  | 31.5 | 30.2 ± 2.15 | 2620 ± 221.6 | 672 ± 81.7 |
| Control | 0 (NaCl) | 25.9 ± 2.09 | 1533 ± 146.3 | 551 ± 24.4 |
| Nifedipine | 0.315 | 24.0 ± 0.83 | 1622 ± 128.5 | 537 ± 52.8 |
|  | 1.0 | 26.5 ± 1.91 | 1994 ± 257.5 | 585 ± 35.1 |
|  | 3.15 | 25.9 ± 1.31 | 2209 ± 121.5 | 601 ± 40.0 |
|  | 10.0 | 27.0 ± 1.78 | 2436 ± 262.3 | 671 ± 69.8 |
|  | 31.5 | 27.8 ± 2.25 | 2832 ± 82.0 | 656 ± 86.8 |
| Control | 0 (NaCl) | 28.9 ± 1.71 | 2358 ± 199.9 | 713 ± 53.8 |
| Nisoldipine | 0.315 | 32.3 ± 1.75 | 2604 ± 221.7 | 747 ± 73.6 |
|  | 1.0 | 28.5 ± 1.28 | 2394 ± 84.3 | 791 ± 79.9 |
|  | 3.15 | 36.4 ± 3.03 | 3451 ± 423.9 | 775 ± 63.1 |
|  | 10.0 | 30.5 ± 2.01 | 2689 ± 244.4 | 655 ± 63.3 |
|  | 31.5 | 32.8 ± 1.96 | 3127 ± 338.1 | 671 ± 70.3 |
| Control | 0 (NaCl) | 23.0 ± 1.41 | 1524 ± 154.8 | 676 ± 61.8 |
| Minoxidil | 0.315 | 20.0 ± 0.91 | 1314 ± 40.7 | 409 ± 52.8 |
|  | 1.0 | 16.8 ± 1.66 | 867 ± 111.3 | 445 ± 43.5 |
|  | 3.15 | 11.5 ± 1.38 | 456 ± 95.4 | 264 ± 37.3 |
| Control | 0 (NaCl) | 25.9 ± 2.09 | 1533 ± 146.3 | 551 ± 24.4 |
| Hydralazine | 1.0 | 26.9 ± 0.43 | 2526 ± 212.2 | 666 ± 52.2 |
|  | 3.15 | 25.9 ± 1.41 | 1755 ± 290.7 | 939 ± 60.3 |
|  | 10.0 | 17.9 ± 2.99 | 847 ± 201.9 | 952 ± 89.3 |

TABLE 2

Diuretic action of nitrendipine in comparison with other commercially available vasodilators (total excretion over 6 hours after administration) on spontaneously hypertensive rats dosed with saline solution (systolic blood pressure: 160–200 mm Hg).
Data: $\bar{x} \pm$ SEM of in each case 6 animals.

| Substance | Dose mg/kg perorally | Urine volume ml/kg/6 hours | Excretion of sodium μmol/kg/6 hours | Excretion of potassium μmol/kg/6 hours |
|---|---|---|---|---|
| Control | 0 (NaCl) | 26.9 ± 1.66 | 2137 ± 510.2 | 922 ± 79.1 |
| Nitrendipine | 0.315 | 24.0 ± 2.84 | 1880 ± 282.6 | 751 ± 80.9 |
|  | 1.0 | 26.1 ± 2.78 | 2638 ± 343.8 | 880 ± 127.1 |
|  | 3.15 | 25.0 ± 2.84 | 2265 ± 297.7 | 818 ± 63.7 |
|  | 10.0 | 32.2 ± 2.62 | 2998 ± 200.5 | 938 ± 40.6 |
|  | 31.5 | 34.5 ± 2.87 | 3262 ± 291.0 | 1079 ± 106.1 |
| Control | 0 (NaCl) | 26.9 ± 1.66 | 2137 ± 510.2 | 922 ± 79.1 |
| Minoxidil | 0.315 | 10.0 ± 1.24 | 555 ± 74.3 | 548 ± 111.5 |
|  | 1.0 | 11.6 ± 2.29 | 784 ± 225.2 | 436 ± 77.8 |
|  | 3.15 | 9.7 ± 0.54 | 446 ± 71.3 | 435 ± 30.5 |
| Control | 0 (NaCl) | 21.7 ± 3.10 | 1838 ± 235.6 | 723 ± 54.3 |
| Hydralazine | 0.315 | 21.7 ± 1.96 | 1697 ± 185.9 | 623 ± 91.7 |
|  | 1.0 | 20.1 ± 3.31 | 1646 ± 322.2 | 618 ± 91.9 |
|  | 3.15 | 22.8 ± 2.31 | 1885 ± 307.2 | 693 ± 44.6 |
|  | 10.0 | 26.9 ± 2.17 | 1347 ± 327.6 | 1304 ± 57.2 |

TABLE 3

Systolic blood pressure following administration of nitrendipine, nifedipine and nisoldipine in comparison with other commercially available vasodilators (maximum effect during 6 hours after administration) on normotensive and spontaneously hypertensive rats. Data in mm Hg, $\bar{x} \pm$ SEM of n ( ) animals

| Substance | Dose mg/kg perorally | Blood pressure, mm Hg normotensive rats | Blood pressure, mm Hg hypertensive rats |
|---|---|---|---|
| Control | 0 | 117.0 ± 1.2 (30) | 174.1 ± 2.5 (29) |
| Nitrendipine | 0.315 | 115.5 ± 2.8 (6) | 167.8 ± 6.4 (6) |
|  | 1.0 | 110.8 ± 1.2 (6) | 156.2 ± 3.8 (6) |
|  | 3.15 | 108.2 ± 3.2 (6) | 131.0 ± 3.5 (6) |
|  | 10.0 | 93.5 ± 1.6 (6) | 101.8 ± 3.6 (6) |
|  | 31.5 | 87.3 ± 2.4 (6) | 93.6 ± 2.5 (5) |
| Control | 0 | 117.0 ± 1.7 (30) | 209.5 ± 4.9 (24) |
| Nifedipine | 0.315 | — | 185.5 ± 5.0 (6) |
|  | 1.0 | 107.0 ± 1.7 (6) | 137.7 ± 7.5 (6) |
|  | 3.15 | 100.2 ± 2.9 (6) | 105.7 ± 2.2 (6) |
|  | 10.0 | 87.7 ± 2.6 (6) | 89.3 ± 4.8 (6) |
|  | 31.5 | 80.2 ± 3.1 (6) | — |
| Control | 0 | 114.3 ± 1.3 (29) | 192.9 ± 4.1 (32) |
| Nisoldipine | 0.315 | 111.5 ± 4.0 (6) | 187.8 ± 7.4 (6) |
|  | 1.0 | 104.5 ± 1.8 (6) | 161.8 ± 7.5 (6) |
|  | 3.15 | 105.7 ± 1.6 (6) | 121.2 ± 6.2 (6) |
|  | 10.0 | 96.0 ± 2.4 (6) | 99.2 ± 6.8 (5) |
|  | 31.5 | 79.8 ± 1.6 (5) | 83.3 ± 6.7 (3) |
| Control | 0 | 117.0 ± 1.6 (30) | 164.5 ± 2.0 (23) |
| Minoxidil | 0.315 | 114.0 ± 2.5 (3) | 166.0 ± 5.4 (6) |
|  | 1.0 | 110.8 ± 2.3 (6) | 144.3 ± 3.0 (6) |
|  | 3.15 | 106.9 ± 2.3 (6) | 110.8 ± 6.7 (5) |
|  | 10.0 | 94.9 ± 3.0 (6) | 97.8 ± 4.8 (6) |
| Control | 0 | 119.5 ± 1.6 (24) | 180.6 ± 2.6 (23) |
| Hydralazine | 1.0 | 119.2 ± 3.5 (6) | 178.0 ± 4.6 (6) |
|  | 3.15 | 97.2 ± 3.3 (6) | 155.3 ± 6.0 (6) |
|  | 10.0 | 82.8 ± 2.2 (6) | 115.0 ± 7.1 (6) |
|  | 31.5 | 68.3 ± 2.6 (6) | 83.0 ± 2.5 (5) |

It is understood that the specification and examples are illustrative but not limitative of the present invention and that other embodiments within the spirit and scope of the invention will suggest themselves to those skilled in the art.

We claim:

1. A method of combating sodium inbalance renal insufficiency in a normotensive patient afflicted therewith comprising administering to such patient a sodium inbalance renal sufficiency-restoring effective amount of a 1,4-dihydropyridine of the formula

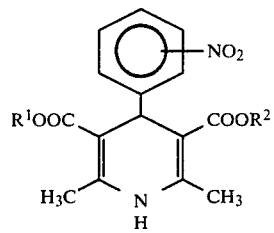

in which $R^1$ and $R^2$ each independently is alkyl with 1 to 4 carbon atoms, and the nitro radical is in the ortho- or meta-position of the phenyl radical.

2. The method according to claim 1, wherein the dihydropyridine is nitrendipine.

3. The method according to claim 1, wherein the dihydropyridine is nifedipine.

4. The method according to claim 1, wherein the dihydropyridine is nisoldipine.

5. The method according to claim 1, wherein the dihydropyridine is administered in about 0.05 to 10 mg/kg of body weight/day.

6. The method according to claim 1, in which $R^1$ and $R^2$ are identical.

7. The method according to claim 1, in which $R^1$ and $R^2$ are different.

* * * * *

UNITED STATES PATENT AND TRADEMARK OFFICE
CERTIFICATE OF CORRECTION

PATENT NO. : 4,582,840

DATED : April 15, 1986

INVENTOR(S) : Bernward Garthoff, et al.

It is certified that error appears in the above-identified patent and that said Letters Patent is hereby corrected as shown below:

Col. 8, line 7            Delete "inbalance" and substitute --balance--

Signed and Sealed this

Nineteenth Day of August 1986

[SEAL]

Attest:

Attesting Officer

DONALD J. QUIGG

Commissioner of Patents and Trademarks